United States Patent
Segalla

(10) Patent No.: US 9,144,572 B2
(45) Date of Patent: Sep. 29, 2015

(54) COMPOSITIONS AND METHOD FOR THE STIMULATION OF THE FEMALE AND MALE SEXUAL RESPONSE

(71) Applicant: Gabriele Segalla, Marcignago (IT)

(72) Inventor: Gabriele Segalla, Marcignago (IT)

(73) Assignee: MULTICHEM S.A.S. DI GABRIELE SEGALLA, Marcignago (Pavia) (IT)

( * ) Notice: Subject to any disclaimer, the term of this patent is extended or adjusted under 35 U.S.C. 154(b) by 0 days.

(21) Appl. No.: 14/446,842

(22) Filed: Jul. 30, 2014

(65) Prior Publication Data

US 2015/0157615 A1    Jun. 11, 2015

(30) Foreign Application Priority Data

Dec. 9, 2013   (IT) .............................. MI2013A2049

(51) Int. Cl.
*A61K 31/44* (2006.01)
*A61K 31/4406* (2006.01)

(52) U.S. Cl.
CPC .................................. *A61K 31/4406* (2013.01)

(58) Field of Classification Search
USPC ........................................................ 514/354
See application file for complete search history.

(56) References Cited

U.S. PATENT DOCUMENTS

| | | | |
|---|---|---|---|
| 3,917,613 A | 11/1975 | Humbert et al. |
| 5,750,108 A | 5/1998 | Edwards |
| 6,322,493 B1 | 11/2001 | Thompson |
| 7,128,930 B1 | 10/2006 | Sacks et al. |

FOREIGN PATENT DOCUMENTS

| | | | |
|---|---|---|---|
| JP | 48005592 B | | 2/1973 |
| JP | 49017579 | * | 5/1974 |
| JP | 49017579 B | | 5/1974 |

OTHER PUBLICATIONS

Ito et al. CAS: 83: 48093, 1975.*
Reach Medical Inc., "Cosmetics containing nicotinic acid menthol ester", 2012, XP002720316.
Database CA, "Menthyl nicotinate", Chemical Abstracts Service, 1984, XP002720317.
Database CA, "Cosmetics containing nicotinic acid menthol ester", 1984, XP002720318.
Italian Search Report, dated Feb. 14, 2014, from corresponding IT application.

* cited by examiner

*Primary Examiner* — Rei-Tsang Shiao
(74) *Attorney, Agent, or Firm* — Young & Thompson

(57) ABSTRACT

Compositions for topical use including menthyl nicotinate as primary active ingredient, in such a dose as to stimulate in a subject the sexual response, preferably in such a dose as to maximize this response in a relative short time, and at least one appropriate lipophilic vehicle so as to solubilize the menthyl nicotinate and allow a rapid absorption thereof in the epithelial tissues of the female and/or male erogenous zones.

12 Claims, 2 Drawing Sheets

*A safe topical cream designed to increase sexual stimulation.*

Ingredients: Deionized Water, Caprylic/Capric Triglycerides, Polyacrylamide c13-14, Isoparaffin/Laureth 7, Citric Acid, SD Alcohol, Vitamin E Acetate, Ginseng Extract, L-Arginine, Phenoxyethanol, Progestreone USP, Vitamin A Palmitate, Lavender Oil, Merhyl Nicotinate

Directions: Apply a small amount, approximately 1/4 teaspoon, of FemPower to fingertips. Apply to the underside of the clitoris and rub in thoroughly for several minutes. Reapply as needed.

Note: The FDA has not evaluated any statement on this tube. The product is not intended to diagnose, treat, cure or prevent any disease Manuactured by
Sarati International, Inc.
Los Fresnos, TX 78566

FIG. 1

COMPOSITIONS AND METHOD FOR THE STIMULATION OF THE FEMALE AND MALE SEXUAL RESPONSE

FIELD OF THE INVENTION

Description

The present invention relates to the use of menthyl nicotinate as a stimulant of the female and/or male sexual response, and/or as intensifying agent of the female and/or male sexual response, and to the relative compositions containing said menthyl nicotinate as primary active ingredient.

More particularly the present invention relates to topical compositions whose primary active ingredient consists of menthyl nicotinate (CAS 40594-65-8; EC Nbr 254-991-1) which acts as vasodilator and is in a mixture with an appropriate lipophilic vehicle and/or with dermatologically acceptable conventional excipients, in order to allow the adequate dosage and application thereof on the female and male genital organs.

BACKGROUND OF THE INVENTION

These compositions, when applied to the clitoris and to the surrounding area, have a marked stimulating and also intensifying effect in respect of female sexuality and, when applied to the penis, have a reinvigorating and retardant effect in respect of the male one.

Female sexual dysfunction (FSD) is quite a common medical condition in women, particularly during the period of the climacteric and of the menopause.

It generally relates to the condition of pain or discomfort during sexual intercourse, reduced vaginal lubrication, delay in arousal and a decrease in sexual desire with consequent difficulty in achieving orgasm, if not even anorgasmy (condition characterised by the reaching of a state of sexual arousal yet with inability to achieve orgasm).

It is by now well known that these symptoms are mostly due to the hormonal changes associated with the period of the menopause, although women also in the premenopausal period, for the most widely varying reasons (anxiety, physical and psychological stress, high blood pressure, illness, vitamin deficiencies, tranquillisers, antidepressants, etc.), can display, albeit temporarily, said symptoms.

The change in the hormonal balances associated with the menopause in particular can lead to reductions in the blood flow, thinning and dryness of the tissues in the genital and urinary system (vagina, bladder, clitoris, etc.) with unpleasant or painful sensations (burning, irritation) during sexual intercourse and, consequently, a decrease in libido, as well as difficulty or inability to reach orgasm or frigidity.

It should be remembered that orgasm, producing a sensation of intense pleasure, has an extremely important function in creating equilibrium in the relationship of the couple, making the woman feel more satisfied and consequently closer to her partner, and also the latter more gratified on a sexual and affective level.

The clitoris, containing more than 6,000 nerve endings, is the erectile and extremely vascularised organ, as well as the most sensitive part of the female body. When stimulated, its nerve endings activate muscle contractions which in turn cause the intense sensation of reaching orgasm. It is by now known to medical science that orgasm, thanks to its ability to increase the levels of oxytocin and to release endorphins, improves the mood, produces a condition of general relaxation and can have beneficial effects on sleep. Moreover it is now established that it burns a considerable quantity of calories and has a positive influence on the functioning of the cardiovascular system, thus contributing to reaching a general state of psychological and physical well-being.

The decline in sexual desire or the inability to reach orgasm are problems found more easily in women than in men.

In men however there are reports of a certain frequency, in addition to the problems due to erectile deficiency of the penis (and therefore to a lack of flow of blood in the corpora cavernosa and in the glans), also of those relating to premature ejaculation, attempts at remedying which have been made with so-called "cooling" or retardant or vasoconstrictor topical preparations, containing, for example, menthol or camphor or benzocaine and similar, all having in fact a slightly anaesthetic effect, i.e. capable of reducing the sensitivity of the glans.

This unfortunately, in some cases, can, in the long term, cause the effect of reducing the supply of blood in the corpora cavernosa and in the glans, thus causing a consequent erectile deficiency of the sexual organ.

Numerous preparations and compositions for topical use for treating female sexual dysfunction (FSD) have been described in the art and are found on the market, mostly based on direct vasodilator agents such as, for example, prostaglandin, papaverine, hydralazine, sodium nitroprusside, phenoxybenzamine, phentolamine, vasoactive neuropeptides, etc.

Similarly described and present on the market are compositions with a base of esters of nicotinic acid such as methyl nicotinate or benzyl nicotinate, also used as direct vasodilator agents, often in association with menthol for moderating the excessive rubefacient effect and the sensation of burning caused by these esters.

However, since menthol is a known vasoconstrictor (see for example the article *"Effect of topical menthol on ipsilateral and contralateral superficial blood flow following about of maximum voluntary muscle contraction"*, IJSPT, Vol. 6, No. 2, June 2011, p. 83), its application on human skin reduces the flow of blood in the part treated topically and the consequent strong sensation of coldness which it causes (also at low concentrations) is the disadvantage associated with compositions known in the art to described hitherto and intended for topical use for stimulating the female and/or male sexual response.

The disadvantage associated with the vasodilator agents used to date in these formulations for the stimulation of the female and/or male sexual response is therefore that of entailing an unpleasant rubefacient and itching effect for which attempts are made to attenuate by introducing other compounds, such as in fact menthol.

It is in fact known that the vasodilator substances indicated above, which boast beneficial effects on the stimulation of the female and male sexual response, can cause in some cases also negative effects such as reddening, erythema and oedema at times with itching, burning, irritations, excessive sensation of heat or cold, etc., also when present in the preparation at very low concentrations, for example in the order of 0.05-0.2%.

In particular methyl nicotinate can in some cases be highly irritating to the skin even at concentrations equal to 0.00137-0.003% as indicated in the publication "Risk profile, *Methyl nicotinate MN*" of the Norwegian Food Safety Authority which in turn reports information on the toxic and local irritating effects indicated in "*Monograph of methyl nicotinate*"-section 2.2 of the Council of Europe, 2008.

This low concentration of use of methyl nicotinate (generally below 0.1%) explains the reason why it appears very often as last ingredient or among the last INCI ingredients in many topical compositions.

There are also other types of compositions for topical use intended for the same application of those described above but without a direct vasodilator, which make use of L-arginine which in itself is not a direct vasodilator but simply the precursor of a vasodilator compound (NO: nitric oxide).

Since the L-arginine (or its esters) can notoriously (see for example U.S. Pat. No. 7,128,930) give rise to the formation of peroxides and specifically peroxynitrites, these compositions can also cause negative effects and have necessarily to contain antioxidant substances in order to moderate and/or prevent, at least partially, the damage caused to tissues by the peroxides which can be generated by the L-arginine itself.

U.S. Pat. No. 6,322,493 describes an applicator of a stimulating composition for the clitoris based on L-arginine used from 1 to 10% in combination with 0.5-5% menthol which acts as vehicle for facilitating and promoting the absorption of L-arginine through the mucous membranes.

It is therefore highly desirable to have available compositions intended for stimulation of the female and/or male sexual response which do not exhibit the disadvantageous phenomena of a strong sensation of cold, cooling and/or decrease in the flow of blood associated with the use of menthol nor the effects of reddening, itchy oedema, sensation of burning, irritations, reddening or=hyperaemising effect associated with the use of "aggressive" vasodilators such as for example the common aforementioned methyl nicotinate.

The use of methyl nicotinate is known in cosmetic compositions for the treatment of the hair and of the skin: however as far as the Applicant is aware the use of menthyl nicotinate as stimulating agent for treating female sexual dysfunction (FSD) and/or as intensifier of the female and/or male sexual response is not known.

Even if included among the INCI ingredients of an advertising web page relating to the stimulating cream "Fem Power" of the company Sarati (Reach Medical, Inc.: "Fem Power", 31 May 2012, Retrieved from the Internet: www.intimatehealth.com/Fempower.htm [retrieved on 2014-02-14]), the Applicant has found that menthyl nicotinate is not really contained in said cream and that its mention among the ingredients listed on the aforesaid web page is instead a printing error of the term "methyl nicotinate", as shown by the actual INCI composition given on the tube of said cream purchased by the Applicant, the photo whereof is attached to the present Application (FIG. 1).

Moreover this "Fem Power" cream contains, in addition to the methyl nicotinate, also L-arginine among the active ingredients and therefore also has the disadvantage of generating peroxides which could cause damage to the tissues as reported above.

SUMMARY OF THE INVENTION

The object of the present invention is that of overcoming, at least in part, the disadvantages of the prior art by providing compositions for topical use for the stimulation and/or the increase in the female and/or male sexual response which are alternative, if not even improved, with respect to those known.

Another object of the invention is that of providing a new preparation for topical use capable of stimulating a strong and intense sexual response, both female and male, without however exhibiting the disadvantages or the negative effects of other preparations containing methyl or benzyl esters of nicotinic acid (niacin).

These and other objects are achieved by the compositions for topical use in accordance with the invention having the features listed in the annexed independent claims.

Advantageous embodiments of the invention are disclosed by the dependent claims.

One object of the present invention relates to the use of menthyl nicotinate as active agent able to stimulate the female and/or male sexual response in topical applications, which can be used as single primary active agent or in combination with other active agents having activity of topical stimulating of the female and/or male sexual response.

Another object of the present invention relates to compositions with topical use having activity functional to the stimulating of the female and/or male sexual response, and/or in the increasing of the intensity of said response, also up to the maximisation thereof, containing menthyl nicotinate, in such a dose as to cause in the individual the maximum sexual response, in a relatively short time, with minimum toxicity.

Yet a further object of the present invention relates to a method for significantly increasing both the female and male sexual response by applying on the clitoris and neighbouring tissues or on the glans of the penis the aforesaid composition, in the form of creamy emulsion, gel (hydrogels, lipogels, gel creams of various consistency including a fluid one), ointment, pomade, oleolite or lotion.

The menthyl ester of the nicotinic acid, i.e. the ester resulting from the reaction of the nicotinic acid (also known as niacin or vitamin B3 or vitamin PP) with the menthol, has the following molecular structure:

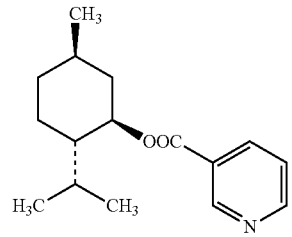

Molecular formula: $C_{16}H_{23}NO_2$
INCI name: Menthyl nicotinate
Other chemical names: 5-Methyl-2-(isopropyl) cyclohexyl nicotinate; (2-propan-2-ylcyclohexyl) 5-methylpyridine-3-carboxylate.
CAS Nbr. 40594-65-8; EC Nbr 254-991-1.

Said compound is a known active ingredient used in creams and gels for the cosmetic treatment of the skin (i.e. for maintaining it in good condition), of cellulite, in lotions for the treatment of hair loss, and also as ingredient of some toothpastes and mouthwashes.

In fact the esters of nicotinic acid and nicotinic acid itself are all direct vasodilators, which therefore do not generate nitrogen oxides nor any damaging peroxides as instead occurs for L-arginine.

Moreover the menthyl nicotinate, in the concentrations provided by the present invention, does not exhibit any unpleasant rubefacient and itching effect, making therefore useless, if not even disadvantageous, the addition of other soothing or anti-itching compounds, such as in fact menthol.

Therefore the menthyl nicotinate can be used alone as primary agent, even if this is not binding for the purpose of the present invention.

The menthyl nicotinate can be prepared according to methods known in the art, in particular by means of transesterification, such as for example that described in U.S. Pat. No. 3,917,613 or that described in "*Transesterification of methyl esters of aromatic and α, β-unsaturated acids with bulky alcohols*: (−)-*menthyl cinnamate and* (−)-*menthyl nicotinate*", Organic Syntheses, Coll. Vol. 8, p. 350 (1993); Vol. 68, p. 155 (1990), performing a possible subsequent distillation to remove the menthol which has not reacted and obtain a highly pure menthyl nicotinate where its purity is essential for its use.

The Applicant has unexpectedly found that said menthyl nicotinate is also an effective stimulant of the female and/or male sexual response, also capable of increasing said female and/or male sexual response and even of maximising it, in the absence of other stimulating agents known in the art, being therefore capable of acting, on the physiology of the female and/or male sexual response, without the need for the addition of other coadiuvating active ingredients.

In fact it has been found by the Applicant that the menthyl ester of the nicotinic acid exerts, alone and in quantities of at least 0.5% by weight up to 5% by weight of the same, in women:
Intense and prolonged stimulation of the clitoris.
A pleasing sensation of freshness and of warmth.
A pleasing and intense turgidity of the tissues on which the preparation is applied without however causing annoying reddening or itching.
A pleasing sensation of cool tingling in the zone of application which, according to the individuals and the concentration of the active ingredient, can be perceived also up to one hour and more after application.
A stimulating sensation of warmth and freshness simultaneously.
Decrease in the times of foreplay (period necessary for preparing the woman for the sexual act).
Decrease in the latency period (i.e. the period of time between orgasms).
Decrease in the time necessary for reaching orgasm.
Multiple orgasms.

In men:
Greater ability to exert voluntary control of ejaculation.
A greater flow of blood in the corpora cavernosa and consequently a greater turgidity and power of erection.
A more intense sexual stimulation.
A pleasing sensation of freshness and of warmth.
A pleasing and intense turgidity of the tissues on which the preparation is applied without however causing annoying reddening or itching.
A pleasing sensation of cool tingling in the zone of application.
A stimulating sensation of warmth and freshness simultaneously.
A retardant and at the same reinvigorating effect.

The compositions of the invention, which do not need menthol and/or methyl nicotinate, contain also at least one appropriate lipophilic vehicle dermatologically and/or pharmacologically acceptable, suitable for solubilising the menthyl nicotinate and suitable for application on the epithelial tissues of the genitals, so as to allow an effective and safe skin absorption of the menthyl nicotinate itself.

Said lipophilic vehicle is preferably selected from the group of adipates, laurates, caprates, myristates, cocoates, hydrogenated oils, optionally ethoxylated, or mixtures thereof; more preferably selected from among (INCI name) dibutyl adipate, hexyl laurate, coco-caprylate/caprate, isopropyl myristate, PEG-7 glyceryl cocoate, PEG-40 hydrogenated castor oil, mineral oil, or mixtures thereof.

It is understood that several vehicles as defined above can also be present in the same composition.

Preferably the concentration of menthyl nicotinate in the compositions of the present invention is of the order of 0.5-3%, more preferably of 1-2% by weight.

The formulations of the present invention can also contain one or more different excipients, dermatologically and/or pharmacologically acceptable for topical administration, in a quantity q.s. to 100.

These excipients are the common ones used for the manufacture of creams, gels, ointments, etc. such as for example emulsifiers (for example Peg-7 glyceryl cocoate or PEG-44/Dodecyl glycol copolymer or Hydroxyoctacosanyl hydroxystearate), surfactants (for example polysorbate-80), solubilising agents (for example PEG-40 hydrogenated castor oil, in order to solubilise the menthyl nicotinate in the aqueous phase of the formulation), gelifying agents such as for example carbomer or polyacrylamide $C_{13-14}$ isoparaffin, laureth-7 or acrylates/$C_{10}$-$C_{30}$ alkyl acrylate crosspolymer), suspending agents (for example mineral oil gelified by polyethylene), humectants (such as for example propylene glycol or glycerine), emollients (such as for example rice bran oil or sweet almond oil), pH modifiers (for example lactic acid, triethanolamine), perfumes, colorants, flavourings, preservatives (for example sodium benzoate, potassium sorbate), antioxidants (for example vitamin E acetate), amplifiers of skin absorption (such as for example dimethylsulfoxide—DMSO), coadiuvating vegetal extracts (such as for example ginseng glycolic extract or aloe vera gel) and other additives.

The compositions of the present invention are therefore formulated so as to be dermatologically and/or pharmaceutically acceptable for topical application.

The advantage of the use of the MENTHYL ester of the nicotinic acid, used as primary agent in the compositions of the present invention, is that of not producing, in the doses suggested by the present invention, any unpleasant or painful side effect (such as for example sensations of strong burning, excessive hyperaemisation of the parts on which said preparations are applied, annoying itching, etc.) unlike the preparations containing METHYL, ethyl or benzyl esters of nicotinic acid (niacin) which entail an excessive hyperaemising effect (a local increase in the quantity of blood in an area of the body) and the sensation of burning (as already described in the publications indicated above), all effects these which are not instead found in the compositions which are the object of the present invention.

The peculiar and pleasing sensations (simultaneous fresh-warm) caused by the application of concentrations also relatively high (of the order of 1-2% by weight) of the menthyl nicotinate compound on the skin can easily be explained by hypothesising that a part of the molecule (the nicotinic functional group) tends to exert on the tissues an evident vasodilator effect (typical of the common nicotinic esters) which is however here, so to speak, "modulated" (for a sort of "intramolecular quenching") by the refreshing and vasoconstrictor effect of the other molecular component (the functional menthyl group) thus reducing or even neutralizing the excessive hyperaemising effect and the sensation of burning.

Moreover the sensation caused by the "menthyl" intramolecular part of menthyl nicotinate is completely different from that exerted by the free menthol in the known formulations: in fact this part determines a pleasing sensation of moderate freshness which is simultaneous to the action of vasodilatation and to the sensation of stimulating warmth caused by the nicotinic part of the molecule, in this way making the resulting effect absolutely unique (the aforementioned "cool tingling" effect), not comparable to that which could be achieved with a preparation containing for example menthol+methyl nicotinate.

The main beneficiaries of the topical application of the present compositions are:

A. Anorgasmic female individuals (frigid or impotent).
B. Female individuals with intermittent anorgasmy.
C. Female individuals seeking a more marked and intense sexual response.
D. Male individuals with problems of premature ejaculation.
C. Male individuals seeking a more prolonged and intense sexual response.

The resulting topical compositions according to the preparation of the present invention are to be applied with a light massage directly on the genitals: in the woman preferably on the clitoral hood, in the man on the glans. The application is preferably carried out 4-5 minutes before intercourse, but can also be repeated during intercourse itself whenever required.

BRIEF DESCRIPTION OF THE DRAWINGS

FIG. 1 shows the actual INCI composition given on a tube of "Fem Power" stimulating cream purchased by the Applicant.

Figure 2:
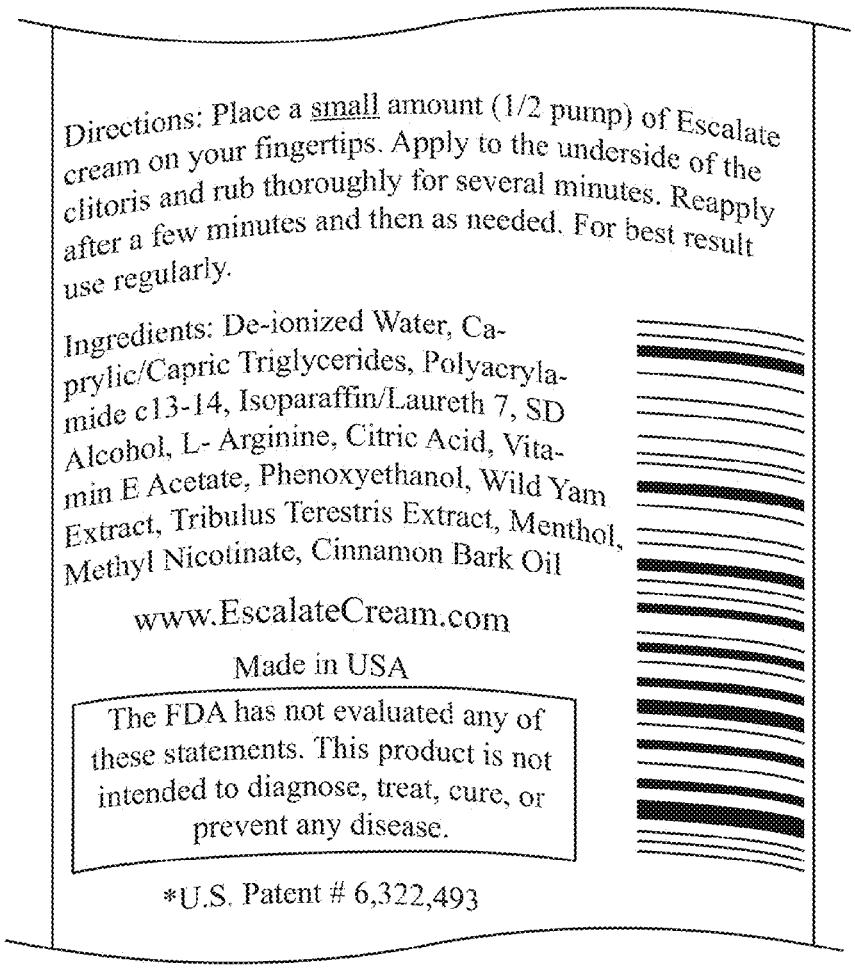
FIG. 2 shows the list of ingredients given on a tube of "Escalate Intimate Enhancing Cream" stimulating cream purchased by the Applicant.

It should be noted that in the preparation for topical use known as "Fern Power", manufactured by the US company Sarati International, given on the web page Reach Medical, Inc. ("Fem Power", 31 May 2012, retrieved on 2014-02-14 Retrieved from the Internet, URL:http://www.intimate-health.com/Fempower.htm), the last component indicated on the same abovementioned web page as "menthyl nicotinate" is in actual fact "methyl nicotinate" as seen also from the website of its producer (Sarati International, http://www.sarati.com/product.php?proid=12;http://www.saratiprivate-label.com/pdf/Fem Power.pdf), as well as on the back of the pack of Fem Power purchased by the Applicant and photographed (FIG. 1 attached to this application) and from the advertising brochure of the manufacturer (which was received together with the product).

Moreover, by accessing the Amazon website, the same product "Fem Power" is on sale, presenting the relative list of ingredients among which "METHYL nicotinate" and not MENTHYL nicotinate appears (see http://www.amazon.com/Sarati-Fempower-Topical-Stimulant-Cream/dp/B000BF1OXG/ref=sr_1_1_?ie=UTF8&qid=1394899200&sr=8-1&keywords=fempower)

Also the preparation with a base of L-arginine and menthol, known as "Escalate Intimate Enhancing Cream" (advertised on the same website of Reach Medical Inc), which is linked to the U.S. Pat. No. 6,322,493 B1 indicated on the packaging, contains "methyl nicotinate" and not menthyl nicotinate, as can be seen from the list of ingredients on the packaging (see FIG. 2 attached to the present application).

Hereinafter some examples of formulation and preparation of the invention are given by way of a non-limiting example. All the percentages indicated are to be understood to be by weight and the components are indicated by their INCI name.

The present invention is not limited to the particular embodiments previously described and illustrated in the annexed examples, but numerous detailed changes may be made thereto, within the reach of the person skilled in the art, without thereby departing from the scope of the invention itself as defined in the appended claims.

EXAMPLES

Example 1

Stimulating gel cream for increasing the intensity of the female orgasm (INCI ingredients)

| | |
|---|---|
| Dibutyl adipate | 8% |
| Polyacrylamide, $C_{13-14}$ Isoparaffin, Laureth-7 | 3% |
| Menthyl nicotinate | 1% |
| Demineralised water | 81.7% |
| Sodium benzoate | 0.3% |
| Propylene glycol | 5% |
| Dimethicone copolyol | 1% |
| Lactic acid (q.s. to pH 4.0-4.5) | |

Example 2

Stimulating gel cream - strong type - retardant and refreshing, for men (INCI ingredients)

| | |
|---|---|
| Demineralised water | q.s. to 100 |
| Glycerin | 3% |
| Propylene glycol | 2% |
| Polysorbate-80 | 0.15% |
| Disodium EDTA | 0.1% |
| Preservatives | 0.3% |
| Antioxidants | 0.05% |
| Carbomer-940 | 0.6% |
| Ginseng glycolic extract | 0.5% |
| Aloe Vera Gel | 3% |
| Coco-caprylate/caprate | 5 |
| Mineral oil | 1% |
| Dimethicone | 0.5% |
| Rice Bran Oil | 5% |
| Vitamin E acetate | 0.2% |
| Fragrance | 0.2% |
| Menthyl nicotinate | 2% |
| Acrylates/$C_{10}$-$C_{30}$ Alkyl Acrylate Crosspolymer | 0.4% |
| Triethanolamine | q.s. to pH 6.0-6.5 |

Example 3

Stimulating, retardant anhydrous lipogel (INCI ingredients)

| | |
|---|---|
| PEG-44/Dodecyl glycol copolymer | 10% |
| Hydroxyoctacosanyl hydroxystearate | 5% |
| Mineral oil gelified by polyethylene | 20% |
| Mineral oil | 50% |
| Methyl salicylate | 5% |
| Isodecyl salicylate | 5% |
| Hydrogenated castor oil | 3% |
| Menthyl nicotinate | 3% |

Example 4

| Delicate fluid hydrogel for repeated applications | |
| --- | --- |
| Demineralised water | q.s. to 100% |
| Preservatives | 0.3% |
| Propylene glycol | 2% |
| Carbomer | 0.7% |
| Menthyl nicotinate | 0.5% |
| PEG-7 glyceryl cocoate | 0.3% |
| PEG-40 Hydrogenated castor oil | 2.4% |
| Triethanolamine | 0.6% |

Example 5

For the purpose of a comparative pre-assessment of the stimulating effect which is to be obtained in relation to the concentration of active ingredient and to pre-assess the consequent sensorial response, the following preliminary test can be performed at different concentrations of menthyl nicotinate before carrying out more substantial clinical tests.

The preparation as per example 1 (but a similar test can take place with all the other preparations described in the following examples) is made in two types of formulations:

a. the formulation as above with the active ingredient (menthyl nicotinate) at a concentration equal to 0.1% (and then to 0.5%, 1%, 1.5%, 2%).

b. the same formulation in blank version, i.e. without active ingredient.

A quantity of for example 0.3 g of the formulation of type a.) is applied, with a light massage, on the front-internal part of the left forearm, near the elbow, and simultaneously the same quantity of the preparation b.) is applied in the same way on the equivalent part of the right forearm.

The difference in intensity of the warm-cold effect and/or of the tingling, of the starting and duration times of the sensorial response between the two zones of application (and therefore between the formulation of type a. with menthyl nicotinate and the formulation b. without menthyl nicotinate) will allow a preparation to be processed and "modulated" in order to meet the specific functional requirements for its final use.

In this way it will be possible to check and evaluate preparations with different concentrations of active ingredient, or at the same concentration of active ingredient but with different secondary vehicle agents, in order to obtain the better tolerated and higher performing formulation (maximum sexual response in a relatively short time span) intended to be possibly experimented and tested in appropriate clinical tests on specific samples of female and/or male subjects.

In fact the "warm-cold" effect on the forearm will be translated into similar sensorial effects, of proportional intensity and therefore easily foreseeable and assessable with respect to the purpose of the present invention.

The invention claimed is:

1. A method for stimulating or enhancing female and/or male sexual response acting on physiology of the female and/or male sexual response, comprising:
administering topically on genital tissues of a female and/or male in need thereof a composition comprising at least 0.5% by weight of menthyl nicotinate as a primary stimulating active agent, and at least one lipophilic vehicle suitable for solubilising the menthyl nicotinate and allowing rapid skin absorption thereof.

2. The method according to claim 1, wherein the composition further comprises at least one excipient.

3. The method according to claim 1, wherein the menthyl nicotinate is 0.5 to 5% by weight of the composition.

4. The method according to claim 1, wherein the menthyl nicotinate is between 0.5% and 3% by weight of the composition.

5. The method according to claim 4, wherein the menthyl nicotinate is between 1% and 2% by weight of the composition.

6. The method according to claim 1, wherein said at least one lipophilic vehicle is selected from the group consisting of adipates, laurates, caprates, myristates, cocoates, hydrogenated oils, optionally ethoxylated, and mixtures thereof.

7. The method according to claim 6, wherein said at least one lipophilic vehicle is selected from the group consisting of dibutyl adipate, hexyl laurate, coco-caprylate/caprate, isopropyl myristate, PEG-7 glyceryl cocoate, PEG-40 hydrogenated castor oil, mineral oil, and mixtures thereof.

8. The method according to claim 1, wherein the composition comprises more than one of said at least one lipophilic vehicles.

9. The method according to claim 2, wherein said at least one excipient is present in quantities q.s. to 100 and is an excipient suitable for compositions selected from the group consisting of creamy emulsions, cream gels, gels, ointments, pomades, oleolites and lotions.

10. The method according to claim 2, wherein said at least one excipient is selected from the group consisting of emulsifying agents, surfactants, solubilising agents, gelifying agents, suspending agents, humectants, emollients, pH modifiers, perfumes, colorants, flavourings, preservatives, antioxidants, skin absorption amplifying agents, coadiuvating vegetal extracts and combinations thereof.

11. The method according to claim 1, wherein the composition is in a form selected from the group consisting of a creamy emulsion; a gel selected from the group consisting of hydrogels, lipogels, and gel creams; an ointment; a pomade; an oleolite; and a lotion.

12. A method for topically stimulating and/or increasing sexual response intensity in females and/or males, up to a maximization thereof, comprising:
administering topically on the epithelial tissues of erogenous zones of a female and/or male in need thereof an effective amount of menthyl nicotinate as a primary stimulating active agent.

* * * * *

UNITED STATES PATENT AND TRADEMARK OFFICE
CERTIFICATE OF CORRECTION

| | | |
|---|---|---|
| PATENT NO. | : 9,144,572 B2 | Page 1 of 1 |
| APPLICATION NO. | : 14/446842 | |
| DATED | : September 29, 2015 | |
| INVENTOR(S) | : Gabriele Segalla | |

It is certified that error appears in the above-identified patent and that said Letters Patent is hereby corrected as shown below:

In the drawings,

Sheet 1, Figure 1, in the list of ingredients, "Progestreone USP" should read --Progesterone USP--.

Sheet 1, Figure 1, in the list of ingredients, "Merhyl Nicotinate" should read --Methyl Nicotinate--.

Signed and Sealed this
Second Day of February, 2016

Michelle K. Lee
*Director of the United States Patent and Trademark Office*